United States Patent
Nord et al.

(10) Patent No.: US 10,166,406 B2
(45) Date of Patent: Jan. 1, 2019

(54) RADIATION TREATMENT PLANNING AND DELIVERY USING COLLISION FREE REGIONS

(71) Applicants: Varian Medical Systems International AG, Cham (CH); Varian Medical Systems, Inc., Palo Alto, CA (US)

(72) Inventors: Janne Nord, Espoo (FI); Joakim Pyyry, Helsinki (FI); Adam Harrington, Glastonbury, CT (US); Sean Herries, San Francisco, CA (US); Joseph Schumm, Seattle, WA (US); Reto Filiberti, Baar (CH); Kari Jyrkkälä, Helsinki (FI); Sylvie Spiessens, Hulste-Harelbeke (BE); Roland Meier, Herzogenbuchsee (CH); Dominique Gasser, Oberrohrdorf (CH)

(73) Assignees: Varian Medical Systems International AG, Cham (CH); Varian Medical Systems, Inc., Palo Alto, CA (US)

( * ) Notice: Subject to any disclaimer, the term of this patent is extended or adjusted under 35 U.S.C. 154(b) by 81 days.

(21) Appl. No.: 15/441,898

(22) Filed: Feb. 24, 2017

(65) Prior Publication Data
US 2018/0243584 A1    Aug. 30, 2018

(51) Int. Cl.
G06K 9/00 (2006.01)
A61N 5/10 (2006.01)

(52) U.S. Cl.
CPC ......... *A61N 5/1039* (2013.01); *A61N 5/1036* (2013.01); *A61N 5/1081* (2013.01)

(58) Field of Classification Search
CPC ... A61N 5/1039; A61N 5/1036; A61N 5/1081
See application file for complete search history.

(56) References Cited

U.S. PATENT DOCUMENTS

| | | | | |
|---|---|---|---|---|
| 7,773,723 B2 * | 8/2010 | Nord | ............... | A61N 5/1031 378/210 |
| 8,175,892 B2 * | 5/2012 | Kapoor | ............... | A61N 5/1048 705/2 |
| 8,986,186 B2 * | 3/2015 | Zhang | ............... | A61N 5/103 600/1 |
| 9,630,026 B2 * | 4/2017 | Froehlich | ............... | A61N 5/10 |

(Continued)

FOREIGN PATENT DOCUMENTS

WO    2016140955    9/2016

OTHER PUBLICATIONS

PCT/EP2018/054350, "International Search Report and Written Opinion", dated Aug. 10, 2018, 14 pages.

*Primary Examiner* — John B Strege
(74) *Attorney, Agent, or Firm* — Kilpatrick Townsend & Stockton LLP

(57) ABSTRACT

Collision free regions are predetermined for one or more class solutions. Each class solution has defined limits for allowed field geometry variations. Collision free regions in planning can be defined as a set of allowed isocenter positions relative to a fixation device. The collision free regions may be visualized by a user to plan for field geometry and isocenter position tradeoffs. Collision free regions in delivery can be defined as a set of allowed couch support coordinates. The treatment fields in a radiation treatment plan can be checked against the collision free regions in delivery to determine whether they will pose any collision risks.

23 Claims, 18 Drawing Sheets

(56) References Cited

U.S. PATENT DOCUMENTS

| | | | |
|---|---|---|---|
| 2009/0003975 A1* | 1/2009 | Kuduvalli | A61N 5/1049 |
| | | | 414/146 |
| 2013/0267830 A1* | 10/2013 | Ojha | A61B 5/055 |
| | | | 600/411 |
| 2013/0289796 A1* | 10/2013 | Bergfjord | A61N 5/1048 |
| | | | 700/302 |
| 2014/0376790 A1* | 12/2014 | Mostafavi | G06T 7/0044 |
| | | | 382/128 |
| 2016/0166855 A1* | 6/2016 | Kumar | A61N 5/1039 |
| | | | 600/1 |
| 2016/0166856 A1* | 6/2016 | Popple | A61B 6/102 |
| | | | 600/1 |
| 2016/0174930 A1* | 6/2016 | Braun | A61B 34/20 |
| | | | 378/205 |
| 2017/0189717 A1* | 7/2017 | MacDonald | A61B 6/032 |
| 2017/0220709 A1* | 8/2017 | Wan | A61N 5/1048 |

* cited by examiner

| Body Measurement | Dimension Value | Reference |
|---|---|---|
| Head Height | 25.91 | Human Factors Design Book |
| Head Breadth | 17.30 | ISO 7250 95th%ile |
| Head Length | 21.30 | ISO 7250 95th%ile |
| Shoulder (bideltoid) Breadth | 55.00 | ISO 7250 95th%ile |
| Chest Breadth | 36.10 | ISO 7250 95th%ile |
| Chest Depth, standing | 27.00 | ISO 7250 95th%ile |
| Stature (body height) | 195.90 | ISO 7250 95th%ile |
| Shoulder Height | 162.50 | ISO 7250 95th%ile |
| Face Length (Naison-menton) | 13.50 | ISO 7250 95th%ile |
| Eye Height (Standing) | 184.20 | ISO 7250 95th%ile |
| Bicep Circumference (relaxed) | 35.10 | FAA Anthropometric Data |
| Pronassle to Back of head – 99th%ile | 24.10 | The Measure of Man and Woman |
| Crown to top nose – 99th%ile | 11.40 | The Measure of Man and Woman |
| Crown to bottom nose – 99th%ile | 17.30 | The Measure of Man and Woman |

*FIG. 12*

RADIATION TREATMENT PLANNING AND DELIVERY USING COLLISION FREE REGIONS

BACKGROUND

Modern radiation therapy techniques include the use of Intensity Modulated Radiotherapy ("IMRT"), typically by means of an external radiation treatment system, such as a linear accelerator, equipped with a multileaf collimator ("MLC"). Use of multileaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, the greater freedom that IMRT and other complex radiotherapy techniques, such as volumetric modulated arc therapy (VMAT), where the system gantry moves while radiation is delivered, and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays) and particles (such as electron and proton beams). While modern linear accelerators use MLCs, other methods of providing conformal radiation to a target volume are known and are within the scope of the present invention.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target, or possibly multiple targets, while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used algorithms to develop and optimize a radiation treatment plan.

When executing a radiation treatment plan using an external-beam radiation treatment system, it is possible that certain field geometries may cause machine-to-machine or machine-to-patient collisions. In such cases, automated execution of the treatment plan may need to be prevented or else accidents may occur. Therefore, it may be desirable to evaluate collision possibilities when planning and delivering a radiation treatment to ensure the safety and usability of a radiation treatment plan.

SUMMARY

According to some embodiments of the present invention, systems, methods, and apparatuses are provided for managing collision risks in planning and delivery of radiation treatment plans. Collision free regions may be predetermined for one or more class solutions. Each class solution has defined limits for allowed field geometry variations, such as allowed gantry angle ranges and allowed couch parameter ranges.

According to some embodiments, the collision free regions in planning can be defined as a set of allowed isocenter positions relative to a fixation device. The collision free regions may be visualized by a user to plan for field geometry and isocenter position tradeoffs. The collision free regions in delivery can be defined as a set of allowed couch support coordinates. The treatment fields in a radiation treatment plan can be checked against the collision free regions in delivery to determine whether they will pose any collision risks.

According to some embodiments, the model used in planning and the model used in delivery may be independent form each other. The model used in planning and the model used in delivery may be designed to work together, so that each model in planning has a corresponding model in delivery. If a plan is valid according to the model in planning, it is likely to be also valid with a corresponding model in delivery.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 12 shows a table including dimension values for a statistical patient model according to an embodiment of the present invention.

TERMS

Figure 1:
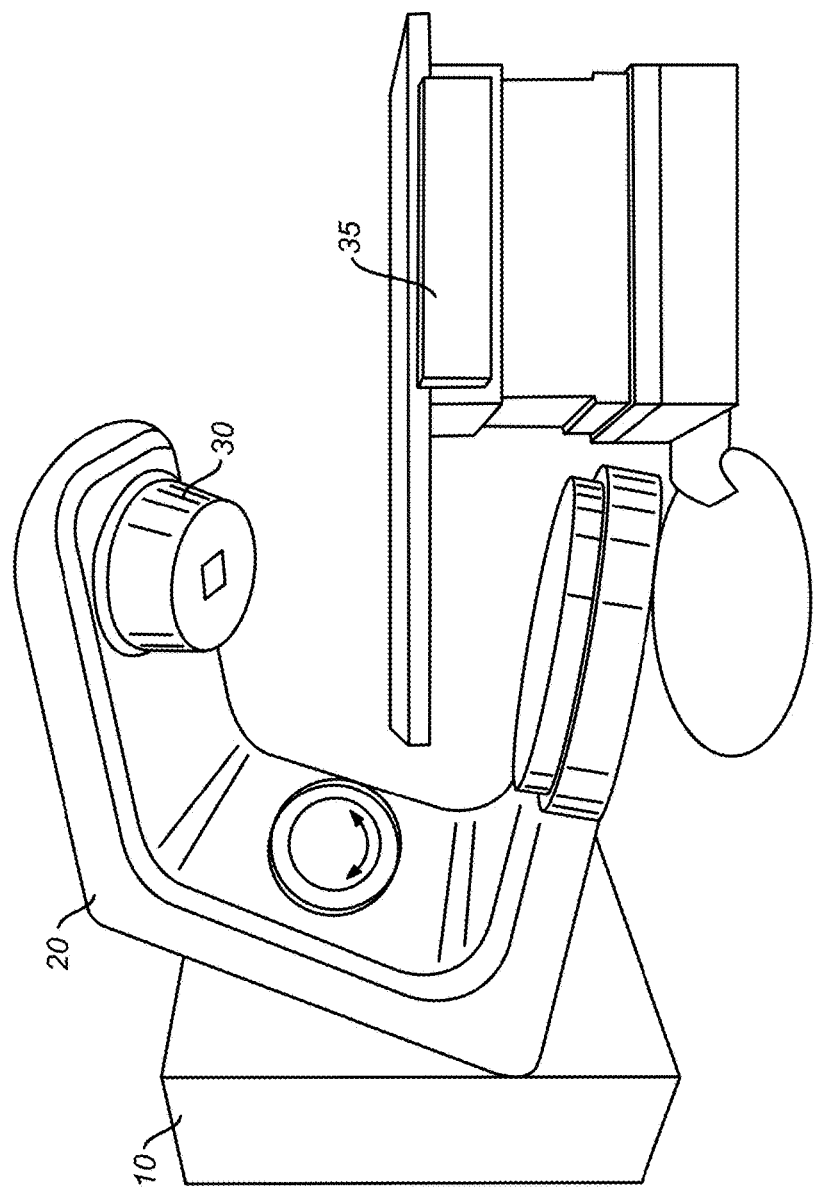
FIG. 1 is a schematic perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "radiation treatment plan" can include a dose distribution, machine parameters for achieving the dose distribution for a given patient, and information about the given patient. A dose distribution provides information about the variation in the radiation dose with spatial positions within a treatment area of the patient. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

"Field geometry" describes the relation between radiation fields, patient, and support devices. Field geometries can be grouped into "class solutions." Each class solution contains limits for allowed field geometry variations, such as allowed gantry angle ranges and allowed couch parameter ranges.

DETAILED DESCRIPTION

The present disclosure relates generally to planning and delivery of radiation treatment using external-beam radiation treatment systems, and is more particularly directed to tools for managing collision risks during planning and delivery of a radiation treatment. Collision free regions may be predetermined for one or more class solutions. A class solution may include the following information: (1) field geometry limits, such as allowed gantry angle ranges and allowed couch parameter ranges; and (2) a corresponding collision free region. Different combinations of field geometries, delivery machine models, and patient models produce the collision free regions. For radiation treatment planning, the collision free region defines a three-dimensional space for allowed isocenter positions. For delivery of a radiation treatment, the collision free region defines a three-dimensional space for allowed couch coordinates. Optionally, a class solution can also include an identifier, which can be used for example to communicate between planning and delivery. The identifier may include information of a specific technology solution, for example a version number.

The collision free regions may be visualized by a user to plan for field geometry and isocenter position tradeoffs. In planning, the system may determine a field geometry based on a desired isocenter position in a patient. For example, the system may consider multiple field geometry alternatives and select one that is allowed based on the shape of the corresponding collision free region. As another example, the system may evaluate collision risks of user-selected fields by checking them against collision free regions corresponding to a given isocenter position. In delivery, the system may evaluate collision risks of the fields of a given treatment plan by checking them against the collision free regions of the delivery machine. The system may prevent execution of the treatment plan upon determining that there is collision risks, or the system may limit the execution of the treatment plan by, for example, removing the fields that can cause collisions. Alternatively, the system may notify a user that one or more fields may cause collisions.

I. Radiation Treatment System

In general, radiation therapy consists of the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used. External beam therapy (EBT), also called external radiation therapy, is a method for delivering a beam or several beams of high-energy x-rays to a patient's tumor. Beams are generated outside the patient (usually by a linear accelerator) and are targeted at the tumor site.

Figure 2:
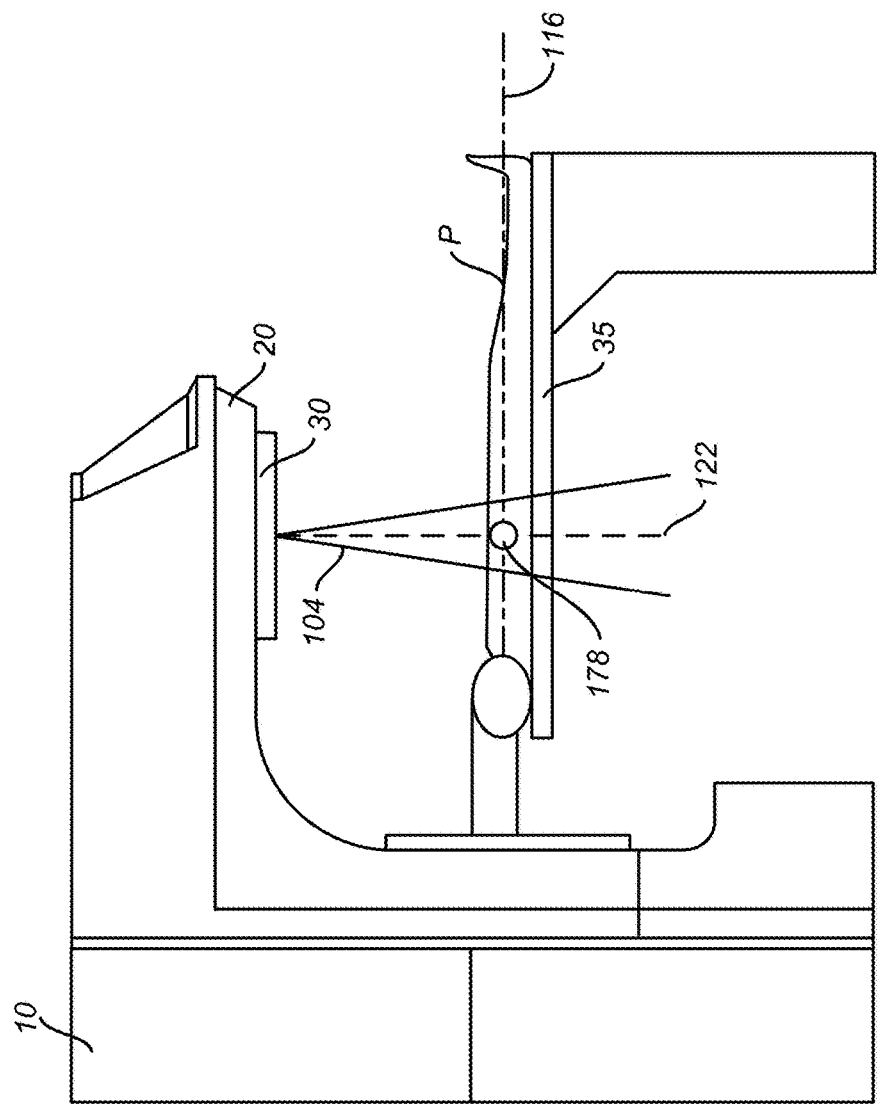
FIG. 2 is a schematic side view of a radiation treatment system.

FIGS. 1 and 2 depict a radiation treatment system of the type that may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type that may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
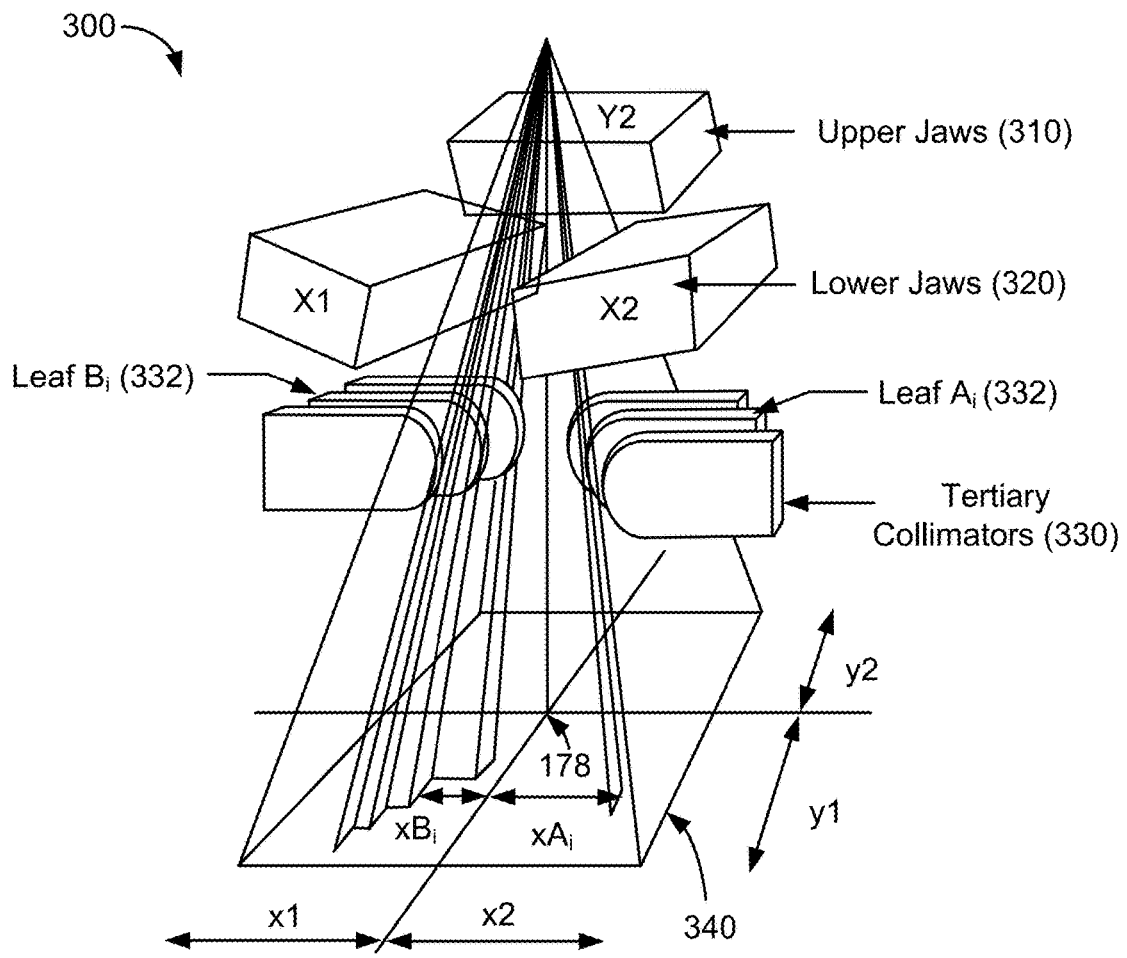
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
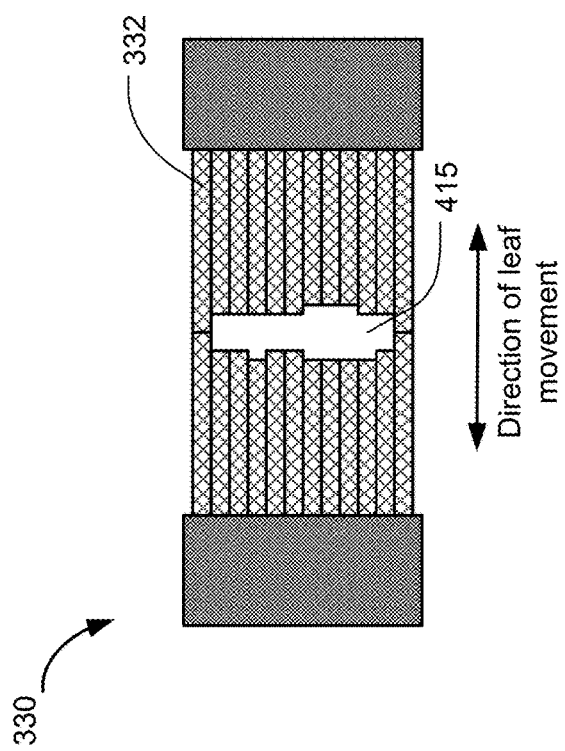
FIG. 4 shows an exemplary multileaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequence of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
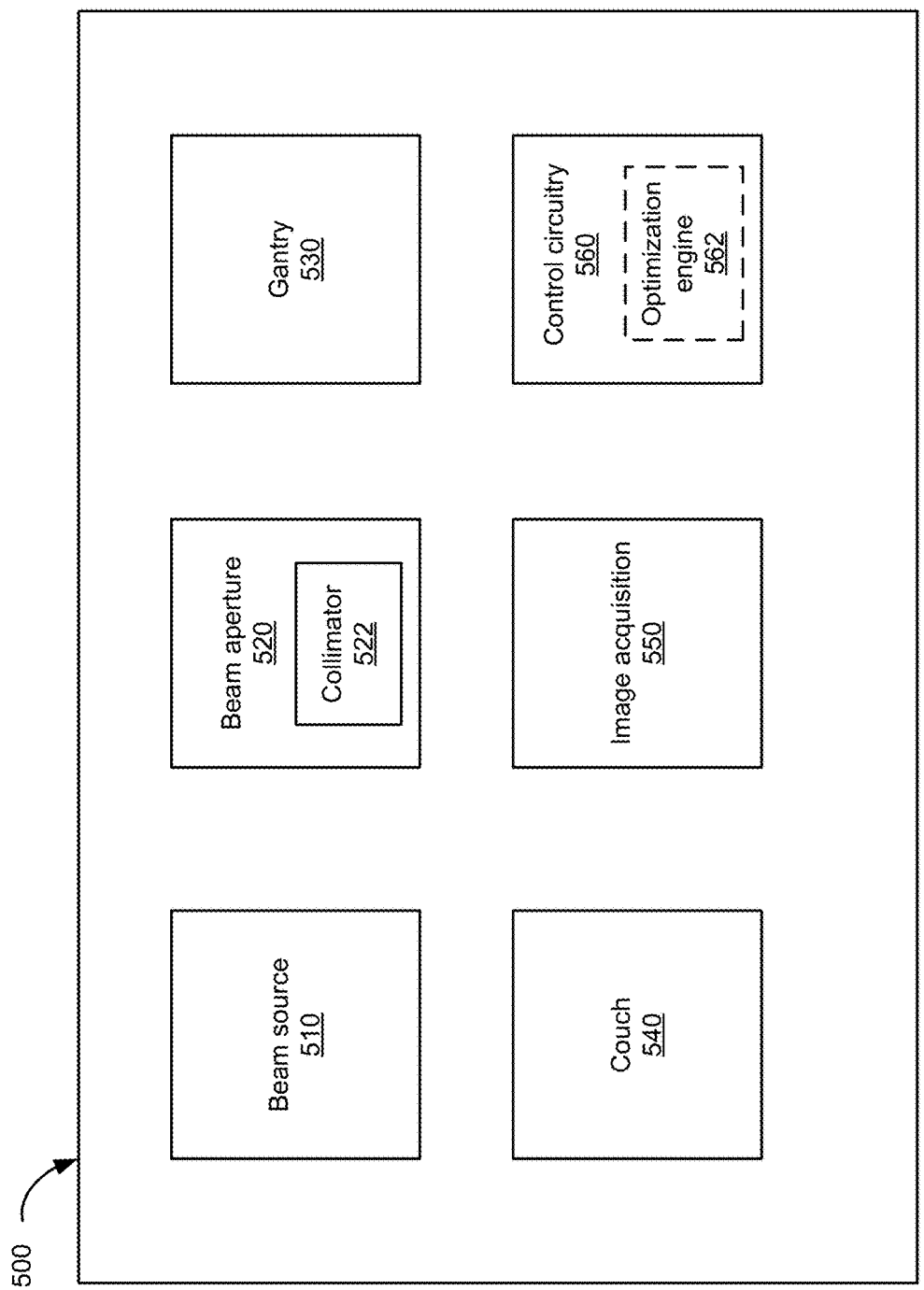
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Plans

Radiation treatment is generally implemented in accordance with a radiation treatment plan that typically takes into account the desired dose of radiation that is prescribed to be delivered to the tumor, as well as the maximum dose of radiation that can be delivered to surrounding tissue. Various techniques for developing radiation treatment plans may be used. Preferably, the computer system used to develop the radiation treatment plan provides an output that can be used to control the external-beam radiation treatment system, including the control points and the MLC leaf movements.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation without risk of damage. This volumetric information along with the prescribed dose limits and similar objectives set by the medical professionals are the basis for calculating an optimized dose distribution, also referred to as fluence map, which in turn is the basis for determining a radiation treatment plan.

A radiation treatment plan, either for radiation therapy or radiosurgery, may include a plurality of treatment fields for delivering radiation to a patient using an external-beam radiation treatment system. The treatment fields may include stationary treatment fields where the direction of incidence to a treatment target is fixed during beam-on, or dynamic treatment fields where the direction of incidence to a treatment target changes during continuous irradiation. A field geometry describes the relation between radiation fields, the patient, and the support devices. In a stationary treatment field, only the MLC leaves and the collimator jaws move, while other treatment axes, such as the isocenter location, gantry angle, couch angles (including rotation, pitch, and yaw), and couch offsets, are fixed during beam on.

Dynamic treatment fields may include, for example, intensity modulated arc therapy (IMAT), volumetric modulated arc therapy (VMAT), and conformal arc therapy. For example, a VMAT treatment may involve one or multiple appropriately optimized intensity-modulated arcs in which radiation is administered with simultaneous gantry rotation and MLC motion. In general, a dynamic treatment field may define a trajectory of some treatment axes of the external-beam radiation treatment system, such as the isocenter location, gantry angle, couch angles (including rotation, pitch, and yaw), and couch offsets.

A VMAT arc can be either coplanar or non-coplanar. A coplanar VMAT arc refers to the case where the couch rotation angle is fixed at zero degree as the gantry rotates during beam-on. A non-coplanar VMAT arc refers to the case where the couch rotation angle is fixed at a non-zero degree angle as the gantry rotates during beam-on, i.e., the couch is not parallel to the axis of rotation of the gantry. Dynamic treatment paths can also include coronal arc, where the gantry is fixed and the couch rotates during continuous irradiation. Dynamic treatment fields enable plans of comparable quality to be delivered in less time.

III. Using Collision Free Regions for Planning Radiation Treatment

When executing a radiation treatment plan using an external-beam radiation treatment system, it is possible that certain field geometries, especially those of dynamic treatment fields, may cause machine-to-machine or machine-to-patient collisions. In such cases, automated execution of the treatment plan may need to be prevented or else accidents may occur. Therefore, it may be desirable to evaluate collision possibilities when planning a radiation treatment to ensure the safety and usability of a radiation treatment plan.

According to some embodiments of the present invention, predetermined collision free regions may be used for planning a radiation treatment to manage collision risks. Collision free regions may be predetermined for one or more class solutions. Each class solution has defined limits for allowed field geometry variations, such as allowed gantry angle ranges and allowed couch parameter ranges. According to an embodiment, a collision free region for planning may be determined for each class solution based on a machine model and a patient model. A statistical patient model, instead of the geometry of an actual patient, may be used. Each collision free region for planning defines a three-dimensional space for allowable isocenter positions for the corresponding class solution. In some embodiments, the collision free regions can be visualized by a user on a computer user interface so that the user can quickly evaluate possible field geometries and any trade-offs between field geometries and the isocenter position.

A. Collision Free Regions and Class Solutions

Figure 6:
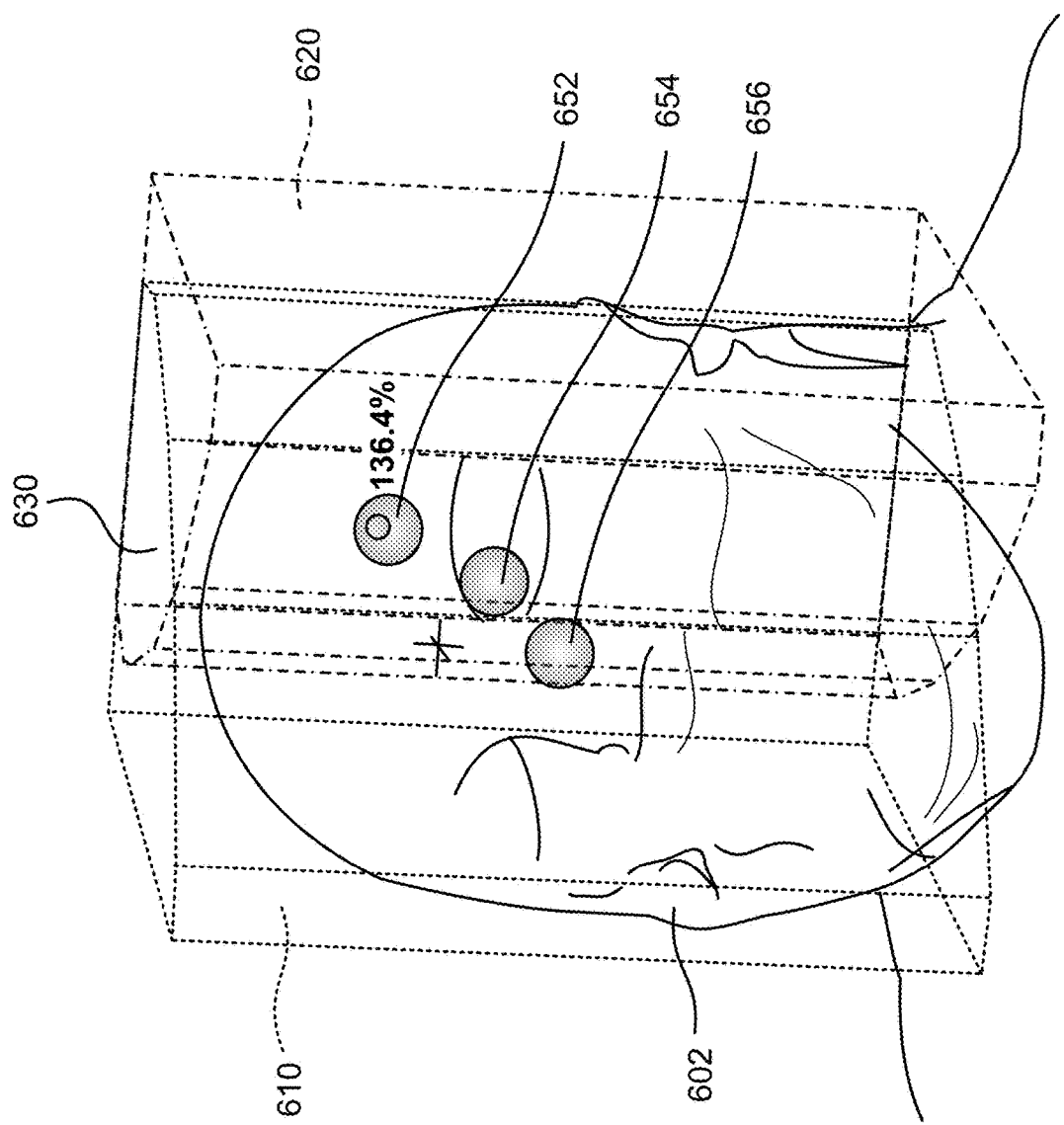
FIG. 6 shows an exemplary user interface that displays some exemplary collision free regions for planning a radiation treatment according to an embodiment of the present invention.

FIG. 6 shows an exemplary user interface that displays some exemplary collision free regions 610, 620, and 630 for planning a radiation treatment. In this example, the radiation treatment is for treating cranial tumors in a patient. A three-dimensional image 602 of the head portion of the patient is superimposed on the collision regions 610, 620, and 630. The image can be, for example, a cone-beam computer tomography (CBCT) image. A first collision free region 610 (indicated by magenta outlines) is on the right hand side of the patient's head. A second collision free region 620 (indicated by cyan outlines) is on the left hand side of the patient's head. The common region in the middle, i.e., the intersection of the first collision free region 610 and the second collision free region 620, may be defined as a third collision free region 630. The three brown balls 652, 654, and 656 are the target volumes (e.g., tumors).

Figure 7:
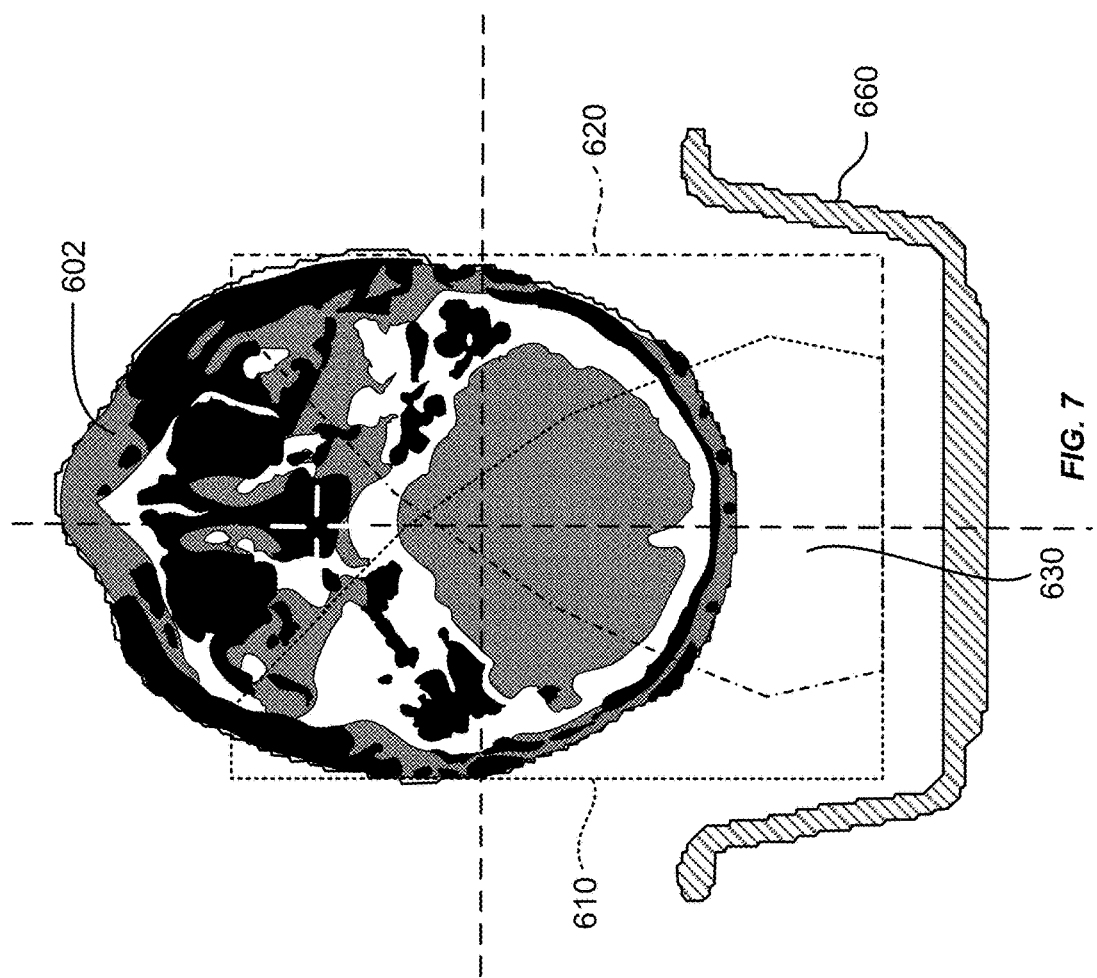
FIG. 7 shows some exemplary collision free regions, as well as an image of a patient, as viewed from the patient's feet, according to an embodiment of the present invention.

FIG. 7 shows the collision free regions 610, 620, and 630, as well as the image 602 of the patient, as viewed from the patient's feet. A model patient support structure 660 (i.e., the U-shaped cyan structure) is also shown in FIG. 7. Although the collision free regions 610 and 620 are shown as boxes, the collision free regions can have more complex geometric shapes, or can be a set of overlapping or non-overlapping shapes according to some embodiments of the present invention.

Each collision free region 610, 620, or 630 is a three-dimensional space for allowed isocenter positions with respect to a corresponding class solution. That is, if the isocenter is positioned anywhere inside a respective collision free region, any field geometries within the limits of the corresponding class solution may be delivered without collision risk.

Figure 8:
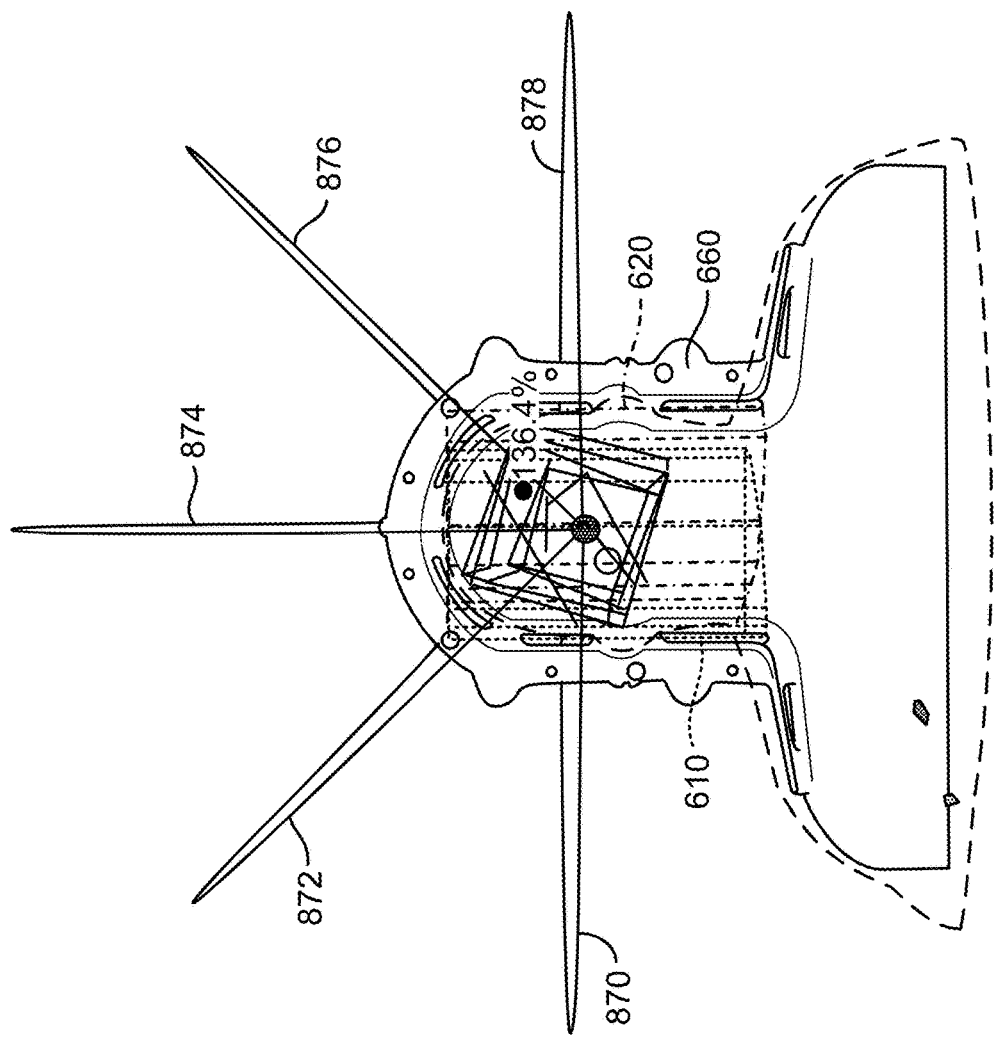
FIG. 8 shows some exemplary treatment fields according to an embodiment of the present invention.

A class solution may include one or more predetermined treatment fields. FIG. 8 shows some exemplary treatment fields according to an embodiment of the present invention. In this example, five arcs 870, 872, 874, 876, and 878 are shown. Each of the five arcs is a half-arc. Among them, the arcs 872. 874, and 876 are non-coplanar arcs, and the arcs 870 and 878 are coplanar arcs. The two half coplanar arcs 870 and 878 may be combined to form a full arc. In other embodiments, more or fewer predetermined treatment fields may be used.

Referring to FIGS. 6-8, according to an embodiment, if the isocenter is placed in the third collision free region 630, i.e., the intersection of the first collision free region 610 and the second collision free region 620, all five arcs 870, 872, 874, 876, and 878 may be delivered without collision risk. If the isocenter is placed in the first collision free region 610 excluding the third collision free region 630, only the arcs 870, 872, 874, and 876 can be delivered without collision risk. If the isocenter is placed in the second collision free region 620 excluding the third collision free region 630, only the arcs 872, 874, 876, and 878 can be delivered without collision risk. Thus, the first collision free region 610 excluding the third collision free region 630 may be associated with a first class solution that includes the predetermined arcs 870, 872, 874, and 876; the second collision free region 620 excluding the third collision free region 630 may be associated with a second class solution that includes the predetermined arcs 872, 874, 876, and 878; and the third collision free region 630 may be associated with a third class solution that includes all five predetermined arcs 870, 872, 874, 876, and 878.

In a radiation treatment, it may be beneficial to place the isocenter in the middle of a target. On the other hand, it may also be beneficial to have more fields (arcs) to distribute the radiation dose in a larger region. When radiation dose is distributed in a larger region from as many directions as possible, the dose level may drop more quickly moving away from a target. Therefore, there may be a trade-off between having the isocenter close to a target and having as many fields as possible. By enabling a user to visualize on a user interface the collision free regions in the same coordinate system as that of the image of the patient, the user may be able to decide more easily the desired isocenter position considering both the isocenter position relative to the targets and the field geometries allowed by each class solution.

Figure 9B:
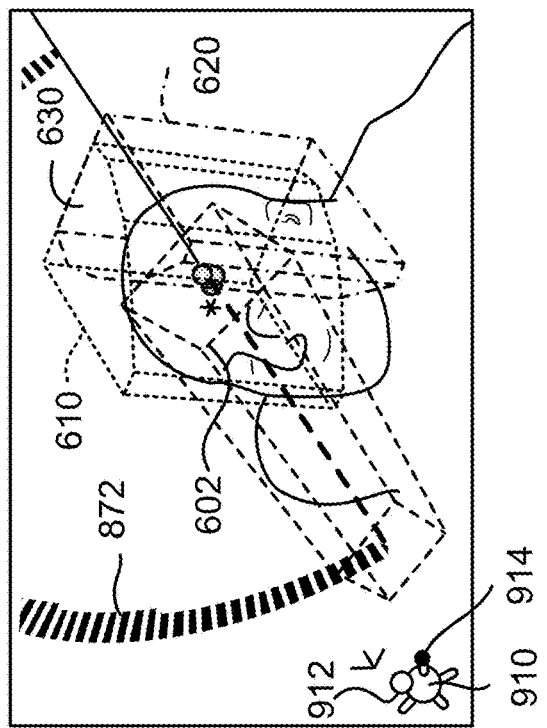
FIG. 9B shows a perspective view of the collision free regions superimposed on the three-dimensional image of the patient as shown in FIG. 9A.
Figure 9A:
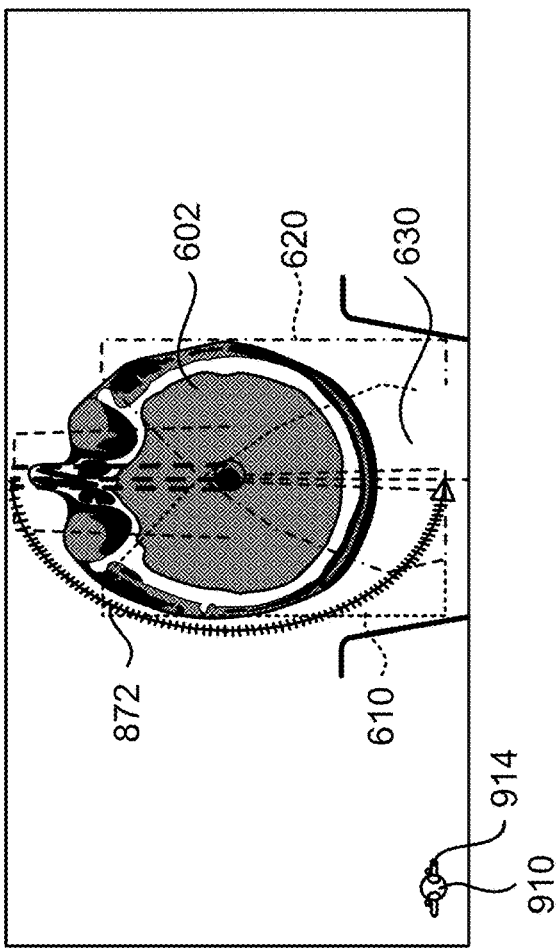
FIG. 9A shows an exemplary user interface where some collision free regions are superimposed on a three-dimensional image of a patient as viewed from the patient's feet.

FIG. 9A shows an exemplary user interface where the collision free regions 610, 620, and 630 are superimposed on the three-dimensional image 602 of the patient as viewed from the patient's feet. The isocenter is placed within the third collision free region 630 (i.e., the intersection of the first collision free region 610 and the second collision free region 620). Thus, all five predetermined arcs 870, 872, 874, 876, and 878 illustrated in FIG. 8 can be delivered without collision risk. FIG. 9A shows the radiation field of one of the arcs 872.

FIG. 9B shows a perspective view of the collision free regions 610, 620, and 630 superimposed on the three-dimensional image 602 of the patient. FIG. 9B also shows the radiation field of one of the arcs 872. Each of FIGS. 9A and 9B also shows a green FIG. 910 on the lower left corner to illustrate patient orientation in the images. The red dot 912 is the patient's nose, and the red ball 914 is in the patient's left hand.

Because the exact patient position is usually not known at planning (i.e., before the patient has been accurately positioned using image guided radiation therapy (IGRT) procedures), certain margins may be provided in determining the shapes of the collision free regions to account for necessary corrections in the patient positioning during delivery.

B. Patient Registration

Figure 10:
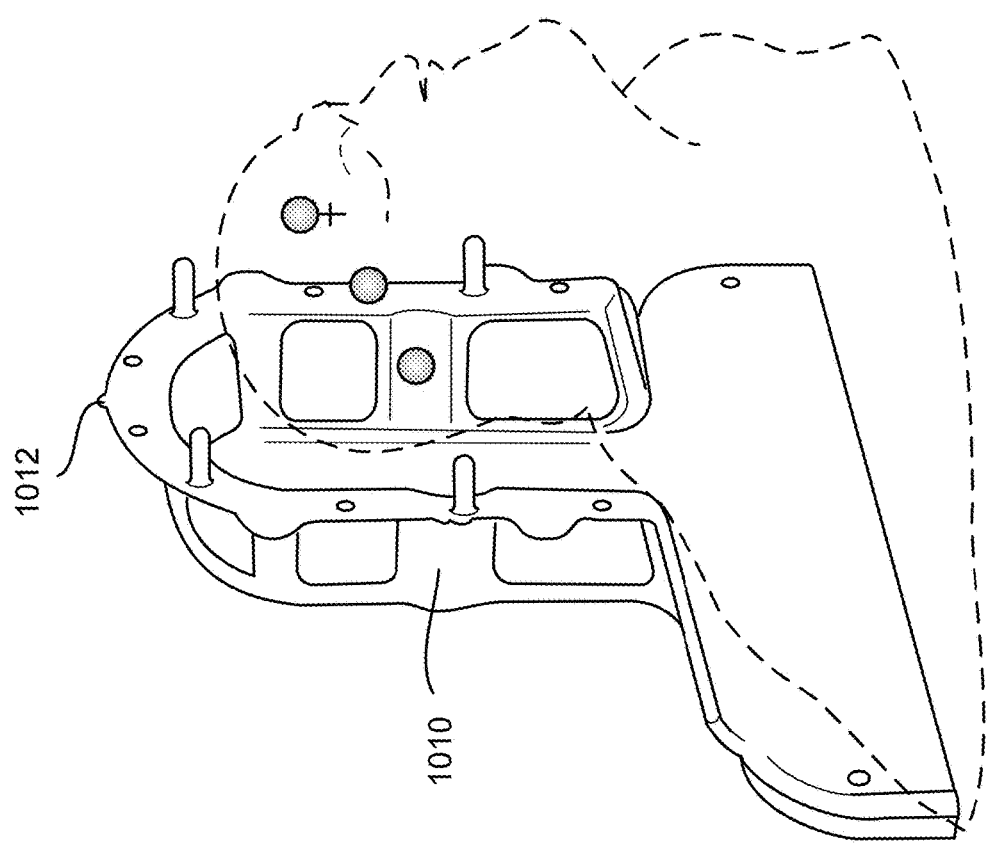
FIG. 10 shows a model fixation device to which collision free regions may be referenced.

When using the collision free regions in planning, a user may need to first register an image of a patient with respect to the collision free regions. According to an embodiment, collision free regions for planning are defined relative to a model fixation device or a patient model that contains a fixation device. FIG. 10 shows a model fixation device 1010 (shown in cyan color), to which collision free regions are referenced. A fixed point on the model fixation device 1010, for example the point "center" 1012, can be used as a reference point.

Figure 11A:
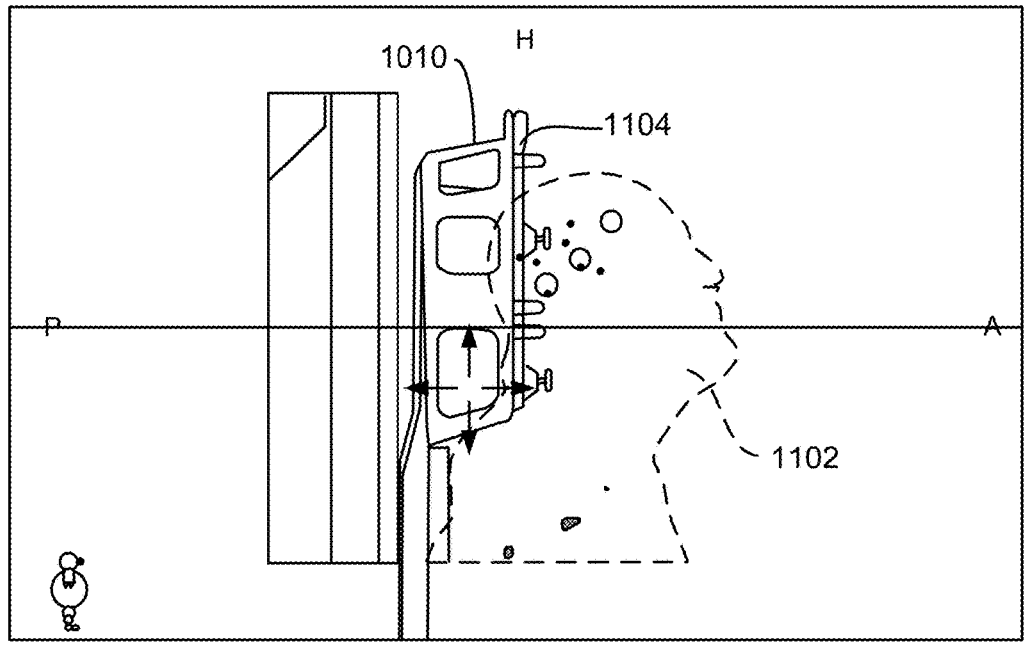
FIG. 11A shows an image of a patient as viewed from the right side of the patient. A couch support device is included in the imaging. A model fixation device is superimposed on the patient's image.
Figure 11B:
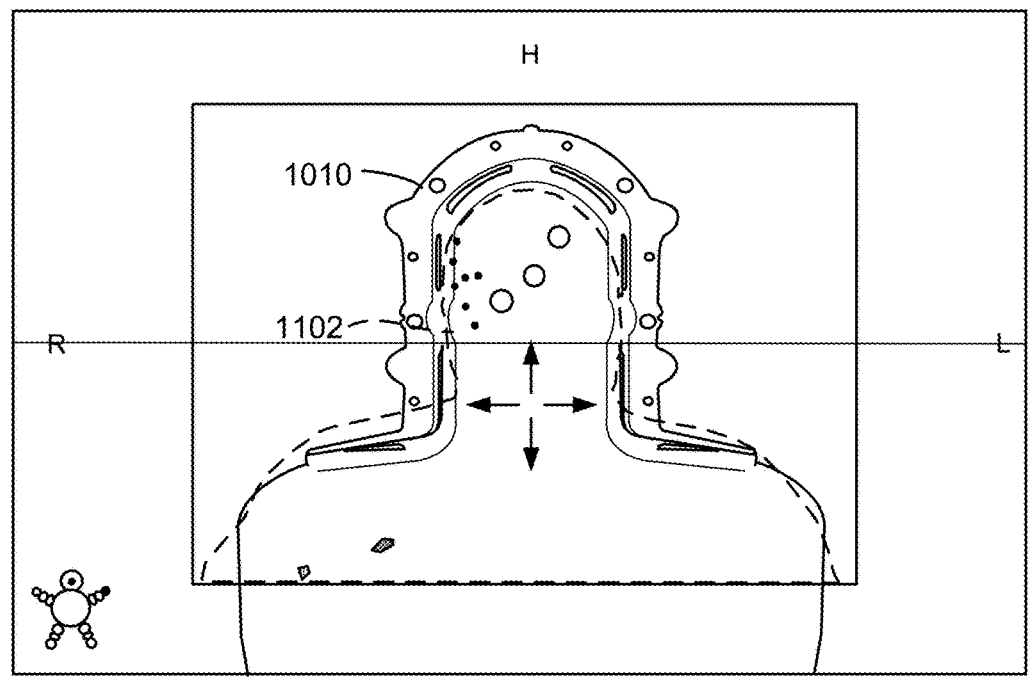
FIG. 11B shows the patient's image superimposed on the model fixation device as viewed from the front of the patient.

FIG. 11A shows an image 1102 of a patient (shown in grey color) as viewed from the right side of the patient. A couch support device 1104 is included in the imaging. A model fixation device 1010 (shown in cyan color) is superimposed on the patient's image 1102. FIG. 11B shows the patient's image 1102 superimposed on the model fixation device 1010 as viewed from the front of the patient. Before a user starts to plan a radiation treatment using the collision free regions, the user may register the patient relative to the collision free regions by aligning the model fixation device 1010 with the image of the couch support device 1104. For example, the user may use the yellow arrows shown in FIGS. 11A and 11B to move the model fixation device 1010 in three orthogonal directions, until the model fixation device 1010 is aligned with the image of the couch support device 1104.

C. Statistical Patient Model

According to an embodiment of the present invention, the shape of the collision free regions may be determined based on a statistical patient model instead of the geometry of an actual patient. A planner (or a delivery person when used in delivery) can estimate whether the geometry of an actual patient fits within the statistical patient model. In some embodiments, the patient model may include a body shape that fits 95% of a patient population. The information for the 95th percentile of a patient population may be taken from the standard ISO 7250. ISO 7250 is a reputable, common, and readily accessible source of information. In one embodiment, a statistical patient model has the dimension values shown in the table of FIG. 12. All dimensions are expressed in units of centimeters unless stated otherwise.

D. Selection of Fields and Isocenter Position

According to an embodiment, a user may be presented with a set of predetermined treatment fields and is allowed to select one or more treatment fields from the set. The set of predetermined treatment fields may be grouped into several class solutions, similar to the example illustrated in FIG. 8 as described above. FIG. 13A shows an exemplary user interface according to an embodiment of the present invention. A schematic FIG. 1310 of a patient, as well as five predetermined arcs 1370, 1372, 1374, 1376, and 1378, are shown in the user interface. The arrow for each arc illustrates the direction of execution. A user can select or deselect an arc by checking the arc on and off. In the example illustrated in FIG. 13A, four of the five arcs (1370, 1372, 1374, and 1376) are selected as shown by the check signs.

Figure 13B:
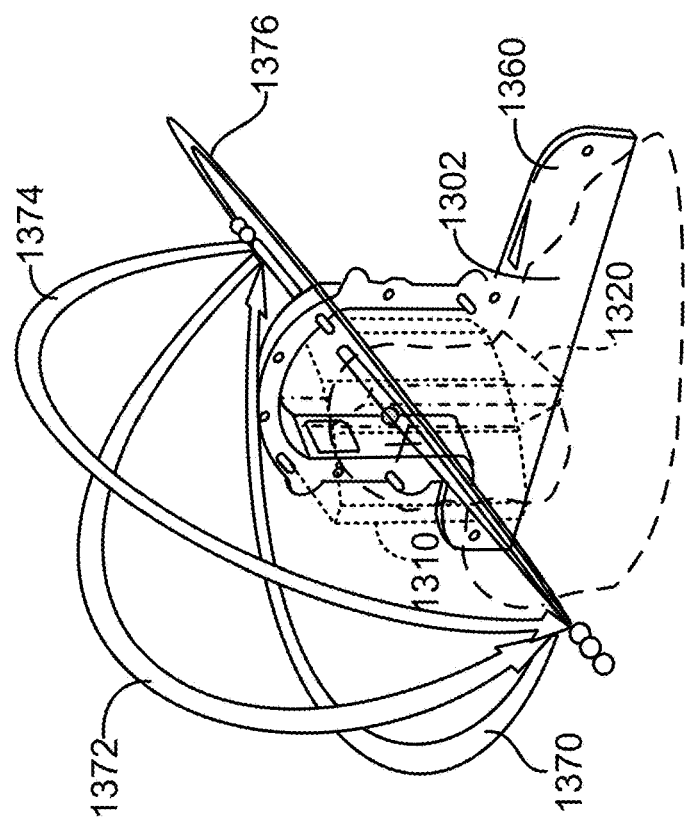
FIG. 13B shows a user interface where some exemplary collision free regions and a model fixation device, as well as an image of a patient, are shown according to an embodiment of the present invention.
Figure 13A:
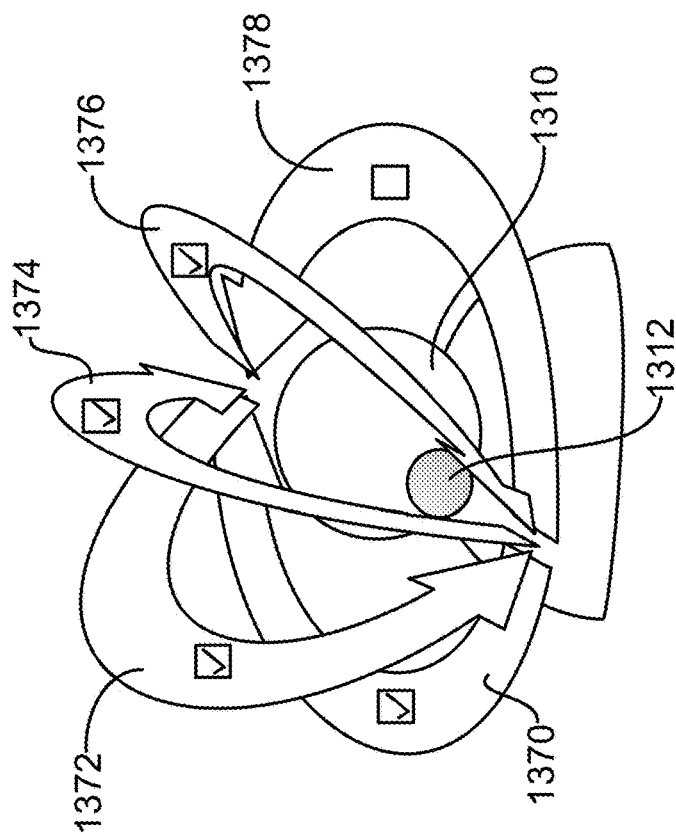
FIG. 13A shows an exemplary user interface where a user may be allowed to select one or more treatment fields from a set of predetermined treatment fields according to an embodiment of the present invention.

FIG. 13B shows a user interface where the collision free regions 1310 and 1320 and the model fixation device 1360, as well as an image 1302 of a patient, are shown. According to an embodiment, if the isocenter is placed in the intersection of the first collision free region 1310 and the second collision free region 1320, all five arcs 1370, 1372, 1374, 1376, and 1378 can be delivered without collision risk. If the isocenter is placed in the first collision free region 1310 or the second collision free region 1320 excluding the intersection region, only a subset of the five arcs 1370, 1372, 1374, 1276, and 1378 can be delivered without collision risk. For example, if the isocenter is placed in the first collision free region 1310 excluding the intersection region, only the arcs 1370, 1372, 1374, 1376 can be delivered without collision risk. Therefore, all four arcs 1370, 1372, 1374, and 1376 selected by the user, as illustrated in FIG. 13A, can be delivered without collision risk. In FIG. 13B, those four arcs 1370, 1372, 1374, and 1376 are shown in the user interface.

In one embodiment, the isocenter position may be manually defined by a user. For example, a user may manually position the isocenter using a user input device (e.g., a mouse) by dragging and dropping the isocenter icon. In other embodiments, the system may automatically calculate a desired isocenter position. For example, the system may calculate the desired isocenter position based on the center of mass of the targets, or a geometrical center point of a smallest box that contains all targets.

According to one embodiment, if the user placed the isocenter position in a collision free region where not all user-selected fields can be delivered without collision risk, the system may allow all the user-selected fields and automatically move the isocenter into a new collision free region where all user-selected fields can be delivered without collision risk. For example, if a user has selected all five arcs 1370, 1372, 1374, 1376, and 1378 shown in FIG. 13A, and has placed the isocenter position in the first collision region 1310 excluding the intersection region, the system may automatically move the isocenter into the intersection region. In one embodiment, the system may move the isocenter to as close to the user-selected isocenter position as possible within the new collision free region.

According to another embodiment, the system may keep the user-selected isocenter position, and automatically remove those fields that cannot be delivered without collision risk. For example, if the user has selected all five arcs 1370, 1372, 1374, 1376, and 1378 shown in FIG. 13A, and has placed the desired isocenter position in the first collision region 1310 excluding the intersection region, the system may keep the user-selected isocenter position, and automatically remove the arc 1378, e.g., by automatically de-selecting arc 1378.

According to yet another embodiment, the system may allow a user to select a desired isocenter position, or the system may select a desired isocenter position (for example based on the center of mass of the targets). The system may then test the selected isocenter position against multiple class solutions and choose one of them. In one embodiment, the system may choose a class solution that includes the most allowed fields for the selected isocenter position. For example, if the selected isocenter position is in the intersection of the first collision free region 1310 and the second collision free region 1320, the system may choose the class solution that includes all five arcs 1370, 1372, 1374, 1376, and 1378 illustrated in FIG. 13A. On the other hand, if the selected isocenter position is in the first collision free region 1310 excluding the intersection region, the system may choose the class solution that includes the arcs 1370, 1372, 1374, and 1376.

It should be noted that a class solution can also include coronal arcs, where the gantry is fixed and the couch coordinate and/or the isocenter moves during continuous irradiation. For such cases, a collision free region for the class solution can comprise a three-dimensional space for allowed initial isocenter positions.

Figure 14:
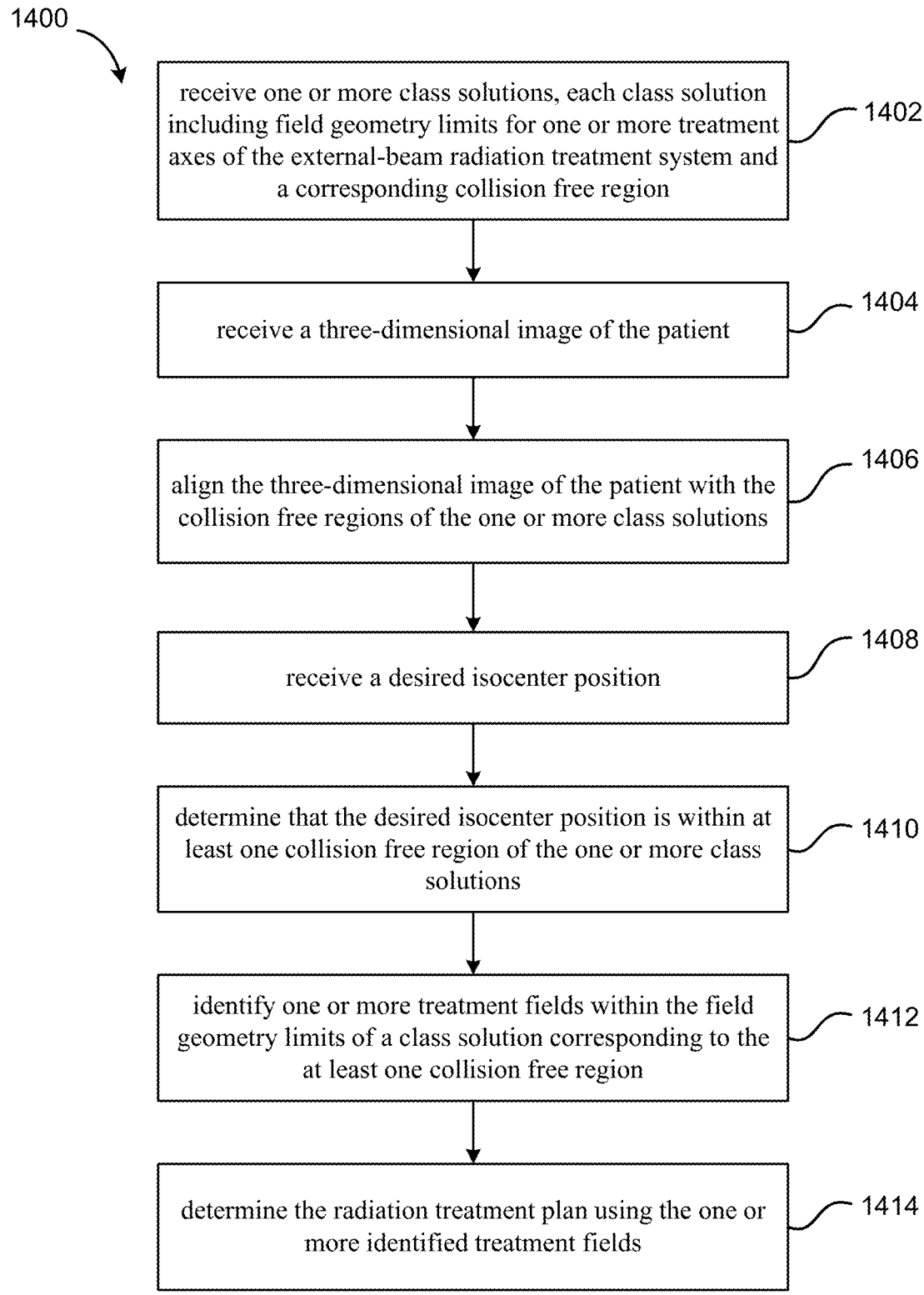
FIG. 14 shows a simplified flowchart illustrating a method of determining a radiation treatment plan for delivering radiation to a patient using an external-beam radiation treatment system according to an embodiment of the present invention.

E. Method of Determining a Radiation Treatment Plan Using Collision Free Regions in a First Embodiment FIG. 14 shows a simplified flowchart illustrating a method 1400 of determining a radiation treatment plan for delivering radiation to a patient using an external-beam radiation treatment system according to an embodiment of the present invention.

At 1402, one or more class solutions are received by a computer system. Each class solution includes field geometry limits for one or more treatment axes of the external-beam radiation treatment system and a corresponding collision free region. The one or more treatment axes of the external-beam radiation treatment system may include, for example, isocenter location, gantry angle, couch angles (rotation, pitch, and yaw), and couch offsets (X, Y, and Z coordinates). The collision free region includes a three-dimensional space for allowed initial isocenter positions determined based on a delivery machine model and a patient model.

At 1404, a three-dimensional image of the patient is received by the computer system. The three-dimensional image can be, for example, a cone-beam computer tomography (CBCT) image. The three-dimensional image of the patient may include image of one or more target volumes within a treatment area of the patient.

At 1406, the three-dimensional image of the patient is aligned with the collision free regions of the one or more class solutions. A user may register the three-dimensional image of the patient with respect to the collision free regions by aligning a model fixation device with an image of a couch support device that is included in the three-dimensional image of the patient.

At 1408, a desired initial isocenter position is received. The desired initial isocenter position may be input by a user using an input device of the user interface. Alternatively, the desired initial isocenter position may be calculated based on a center of mass of the one or more target volumes, or based on a geometrical center point of a smallest box that contains the one or more target volumes.

At 1410, it may be determined that the desired initial isocenter position is within at least one collision free region of the one or more class solutions. For example, the system may compare the desired initial isocenter position against the collision free regions corresponding to the one or more class solutions to determine whether the initial isocenter position falls within the boundary of any collision free region.

At 1412, one or more treatment fields within the field geometry limits of a class solution corresponding to the at least one collision free region are identified. Each class solution may include one or more predetermined treatment fields. In one embodiment, the at least one collision free region includes one collision free region, and identifying one or more treatment fields includes identifying the predetermined treatment fields of the class solution corresponding to the one collision free region. In another embodiment, the at least one collision free region may include a plurality of collision free regions corresponding to a plurality of class solutions, and identifying one or more treatment fields includes selecting a class solution that includes most predetermined treatment fields among the plurality of class solutions.

At 1414, the radiation treatment plan is determined using the one or more identified treatment fields. The radiation treatment plan may include a control-point sequence and a multileaf collimator (MLC) leaf sequence based on the identified one or more treatment fields. The radiation treatment plan may be transmitted to control circuitry of the external-beam radiation treatment system to cause the external-beam radiation treatment system to deliver the radiation to the patient according to the control-point sequence and the multileaf collimator (MLC) leaf sequence of the radiation treatment plan.

Figure 15:
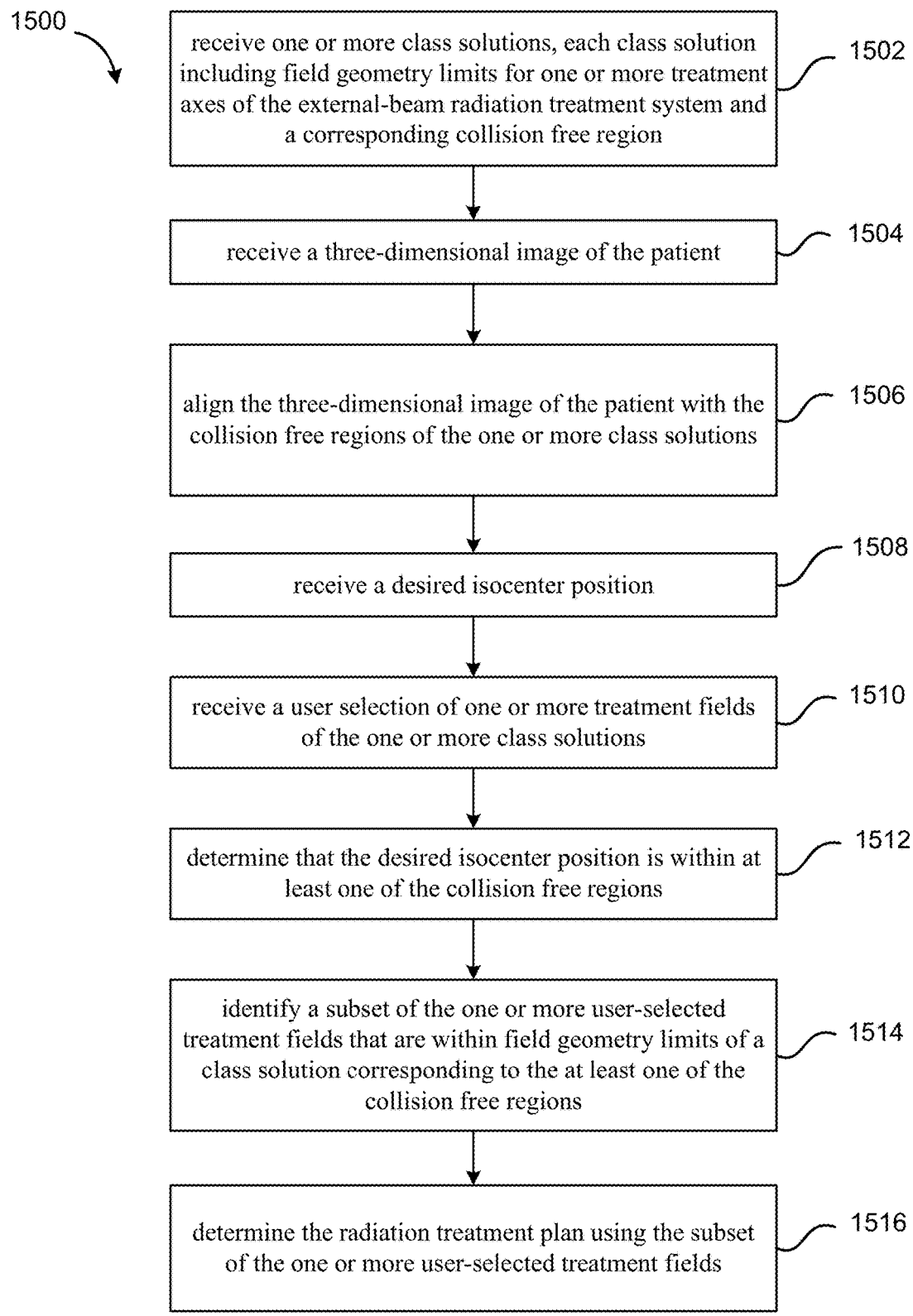
FIG. 15 shows a simplified flowchart illustrating a method of determining a radiation treatment plan for delivering radiation to a patient using an external-beam radiation treatment system according to another embodiment of the present invention.

F. Method of Determining a Radiation Treatment Plan Using Collision Free Regions in a Second Embodiment FIG. 15 shows a simplified flowchart illustrating a method 1500 of determining a radiation treatment plan for delivering radiation to a patient using an external-beam radiation treatment system according to another embodiment of the present invention.

At 1502, one or more class solutions are received by a computer system. Each class solution includes field geometry limits for one or more treatment axes of the external-beam radiation treatment system and a corresponding collision free region. The collision free region includes a three-dimensional space for allowed initial isocenter positions determined based on a delivery machine model and a patient model.

At 1504, a three-dimensional image of the patient is received by the computer system. The three-dimensional image can be, for example, a cone-beam computer tomography (CBCT) image. The three-dimensional image of the patient may include image of one or more target volumes within a treatment area of the patient.

At 1506, the three-dimensional image of the patient is aligned with the collision free regions of the one or more class solutions. A user may register the three-dimensional image of the patient with respect to the collision free regions by aligning a model fixation device with an image of a couch support device that is included in the three-dimensional image of the patient.

At 1508, a desired initial isocenter position is received. The desired initial isocenter position may be input by a user using an input device of the user interface. Alternatively, the desired initial isocenter position may be calculated based on a center of mass of the one or more target volumes, or based on a geometrical center point of a smallest box that contains the one or more target volumes.

At 1510, a user selection of one or more treatment fields of the one or more class solutions is received on the user interface. At 1512, it may be determined that the desired initial isocenter position is within at least one of the collision free regions. At 1514, a subset of the one or more user-selected treatment fields may be identified that are within field geometry limits of a class solution corresponding to the at least one of the collision free regions. In some embodiments, the subset of the one or more user-selected treatment fields may include all of the one or more user-selected treatment fields.

In some embodiments, identifying the subset of the one or more selected treatment fields includes, for each respective treatment field of the one or more user-selected treatment fields, determining whether the respective treatment field is within the field geometry limits of the class solution corresponding to the at least one of the collision free regions. Upon determining that the respective treatment field is outside the field geometry limits of the class solution corresponding to the at least one of the collision free regions, the respective treatment field may be excluded from the subset of the one or more user-selected treatment fields. Upon determining that the respective treatment field is within the field geometry limits of the class solution corresponding to the at least one of the collision free regions, the respective treatment field may be included in the subset of the one or more user-selected treatment fields.

In some other embodiments, upon determining that at least one of the one or more user-selected treatment fields is outside the field geometry limits of the class solution corresponding to the at least one of the collision free regions, the desired isocenter position is moved to a new isocenter position. The new isocenter position is within another collision free region, and all of the one or more user-selected treatment fields are within field geometry limits of a class solution corresponding to the another collision free region.

At 1516, the radiation treatment plan is determined using the one or more identified treatment fields. The radiation treatment plan may include a control-point sequence and a multileaf collimator (MLC) leaf sequence based on the identified one or more treatment fields. The radiation treatment plan may be transmitted to control circuitry of the external-beam radiation treatment system to cause the external-beam radiation treatment system to deliver the radiation to the patient according to the control-point sequence and the multileaf collimator (MLC) leaf sequence of the radiation treatment plan.

IV. Using Collision Free Regions for Delivery of Radiation Treatment

When delivering radiation treatment using a given radiation treatment plan, whether it was planned using collision free regions as described above or planned without using collision free regions, it may be desirable to verify that the field geometries of the radiation treatment plan will be collision free in a specific delivery machine.

A. Collision Free Regions in Delivery

According to an embodiment of the present invention, collision free regions for delivery may be predetermined for one or more class solutions based on the geometries of the actual delivery machine and a patient model. The collision free regions for delivery may take into account delivery specific margins. Each collision free region for delivery defines a three-dimensional space for allowable couch coordinates for a corresponding class solution. That is, if the couch coordinates reside anywhere inside a respective collision free region, any field geometries within the limits of the corresponding class solution may be delivered without collision.

Figure 16:
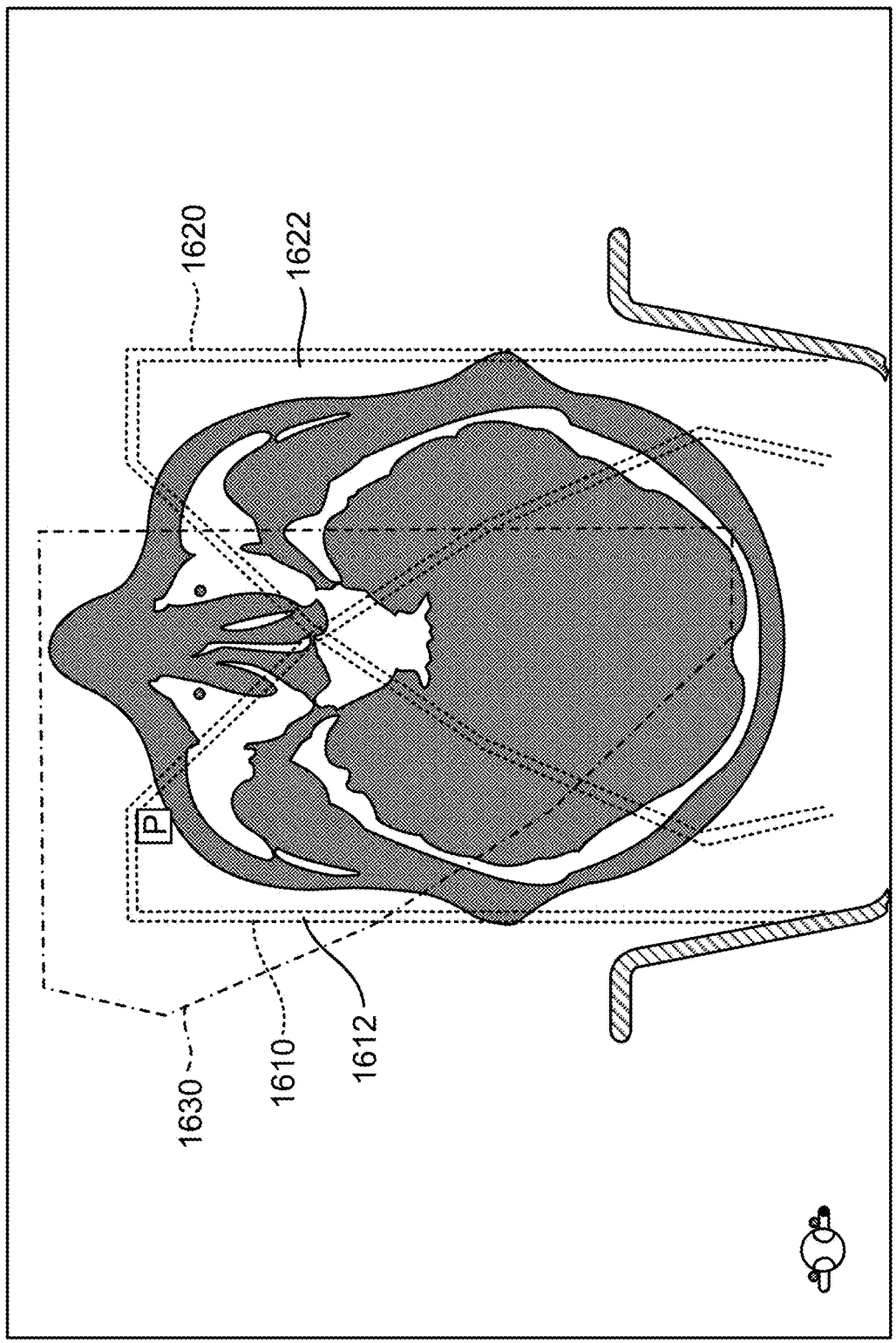
FIG. 16 shows an exemplary user interface for using collision free regions during delivery according to an embodiment of the present invention.

FIG. 16 shows an exemplary user interface for using collision free regions during delivery according to an embodiment of the present invention. The blue outline 1630 indicates a boundary of a collision free region for allowed couch coordinates. Thus, the couch coordinate "A" should be positioned within the blue outline 1630. The inner red outline 1610 indicates the boundary of a collision free region used in planning for allowed isocenter positions. The inner red outline 1612 has some margins subtracted from the outer red outline 1610 giving some space for isocenter corrections during delivery, since the precise patient position is usually not known in planning. Thus, the isocenter "P" should be positioned within the outer red outline 1612 at delivery. The other pair of outer red outline 1620 and inner red outline 1622 indicate the boundary of another collision free region used in planning for allowed isocenter positions.

The model used in delivery may be different from the model used in planning in several ways. First, the collision free regions in delivery may be defined relative to absolute machine parameters, whereas the collision free regions in planning may be defined relative to a model fixation device as discussed above. Second, in delivery, the collision risks are normally evaluated after a patient has been positioned using image-guided radiation therapy (IGRT) procedures, whereas the precise patient position is usually not known in planning. Therefore, larger margins may be provided in the planning model that those provided in the delivery model according to some embodiments. The aim is to make sure that the couch coordinates generated from the planning isocenter after the IGRT position process fall into allowed couch positions in delivery. In the planning stage, some of the information is not available yet. For example, IGRT position shift, as well as pitch and roll corrections, may not be known at planning. The extra margin in planning may ensure that the plan is still deliverable even after the IGRT corrections have been applied.

B. Evaluating Collision Risk of a Treatment Plan

The fields of a treatment plan can be tested against the collision free regions in delivery to evaluate collision risks. In delivery, during the patient positioning using image-guided radiation therapy (IGRT) procedures, a user may have a preview of the couch coordinates and can check whether the couch coordinates fall within any collision free regions, and whether the field geometries and delivery parameters of the treatment plan are within the limits for allowed field geometry variations, such as allowed gantry angle ranges and allowed couch parameter ranges, defined by the class solution corresponding to the collision free region.

In one embodiment, if the delivery parameters are not within allowed limits, the system may prevent the treatment. In another embodiment, the system may notify the user that fields in the treatment plan may cause collision. In a further embodiment, the system may allow the treatment in a limited way. For example, the system may limit the automation of the delivery, such as automatically remove an arc or shorten an arc. The system may also indicate that the treatment axes violate the collision free regions and may indicate the amount of the violation. The system may also indicate the violation of the collision free regions graphically.

C. Collision Free Regions in Planning and in Delivery

The collision free regions for delivery may be independent from the collision free regions for planning. But in some embodiments, class solutions in delivery may be linked to class solutions in planning. That is, each class solution in planning may have a corresponding model in delivery. In one embodiment, an identifier can be used for each class solution to communicate between planning and delivery. The identifier may also identify a specific technology solution, such as a version number. A plan that is collision free according to the model in planning is likely also collision free in the corresponding model in delivery.

By having independent collision free regions in planning and delivery, it may be possible to change the machine to a dosimetrically equivalent machine with different geometric parameters. Sometimes machines are calibrated so that they are dosimetrically equivalent, although the patient support devices may vary. For example, the couch dimensions may be different. Therefore the collision free regions may be different. If a treatment plan is to be delivered with a delivery machine that is different from the model machine used in planning, the delivery machine can evaluate collision risks of the field geometries of the treatment plan against the collision free regions of its own collision model.

In some embodiments, a delivery machine can evaluate collision risks for treatment plans that are not planned with a planning system considering collision free regions. For example, the delivery system may identify that the field geometries of a plan are within a specific class solution. Upon determining that the plan is within the limits of a class solution, certain additional functionality may be enabled. For example, the user may be notified that the plan is within the limits of a class solution. Full automation of the execution of the treatment plan may be enabled upon determining that a plan is within the limits of a class solution. More automation may help to reduce delivery time, which may be especially desirable in radiosurgery applications.

Because the evaluations of collision risks in planning and delivery are independent, changing a machine configuration, such as couch calibration, may not require re-planning or re-evaluation of collision risks. For example, a couch recalibration may affect the absolute couch coordinates and therefore may affect the collision free regions of the target machine. However, a plan that is generated for the previous couch calibration and has been determined to be collision-free is likely to be collision-free for the new couch calibration as well, since the relationship between the collision free regions and the couch coordinates before and after the recalibration should be the same.

D. Method of Delivering Radiation to a Patient Using Collision Free Regions

Figure 17:
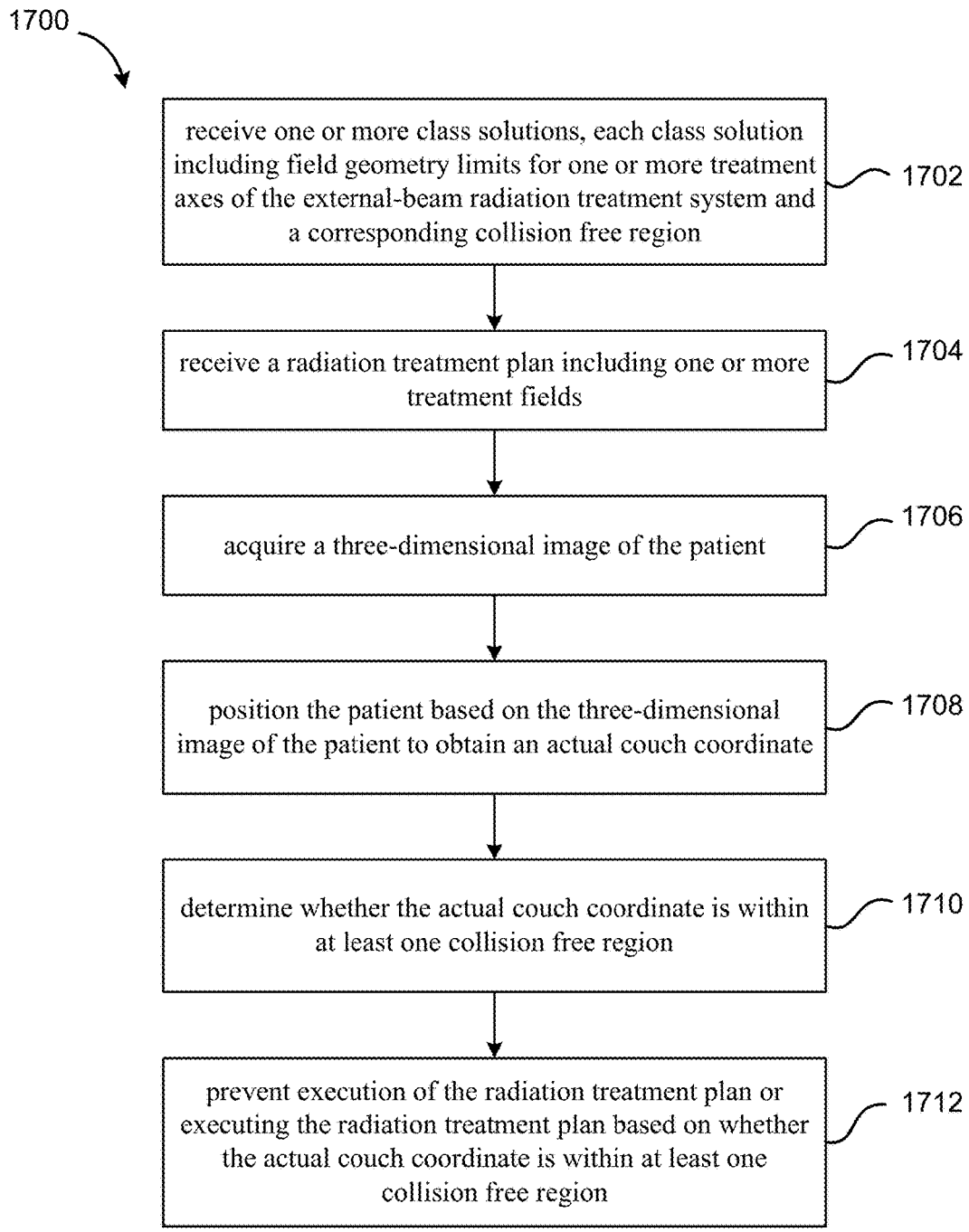
FIG. 17 shows a simplified flowchart illustrating a method of delivering radiation to a patient using an external-beam radiation treatment system according to an embodiment of the present invention.

FIG. 17 shows a simplified flowchart illustrating a method 1700 of delivering radiation to a patient using an external-beam radiation treatment system according to an embodiment of the present invention.

At 1702, one or more class solutions are received by a computer system communicably coupled with the external-beam radiation treatment system. Each class solution includes field geometry limits for one or more treatment axes of the external-beam radiation treatment system and a corresponding collision free region. the collision free region includes a three-dimensional space for allowed couch coordinates determined based on a model of a delivery machine and a patient model.

At 1704, a radiation treatment plan is received by the computer system. The radiation treatment plan may include one or more treatment fields. The radiation treatment plan may be determined using collision free regions or without using collision free regions, as discussed above.

At 1706, a three-dimensional image of the patient is acquired by the external-beam radiation treatment system. The three-dimensional image can be, for example, a cone-beam computer tomography (CBCT) image.

At 1708, the patient is positioned by external-beam radiation treatment system based on the three-dimensional image of the patient to obtain an actual couch coordinate. For example, the patient may be positioned using image-guided radiation therapy (IGRT) procedures.

At 1710, it may be determined whether the actual couch coordinate is within at least one collision free region. For example, the system may compare the actual couch coordinate against the collision regions corresponding to the one or more class solutions to determine whether the actual couch coordinate falls within the boundary of any of the collision regions.

At 1712, execution of the radiation treatment plan may be prevented or performed based on whether the actual couch coordinate is within at least one collision free region.

In some embodiments, upon determining that the actual couch coordinate is not within any collision free region, execution of the radiation treatment plan is prevented. Upon determining that the actual couch coordinate is within at least one collision free region, it may be determined whether the one or more treatment fields of the radiation treatment plan are within the field geometry limits of a class solution corresponding to the at least one collision free region. Upon determining that at least one of the one or more treatment fields of the radiation treatment plan is outside the field geometry limits of the class solution corresponding to the at least one collision free region, execution of the radiation treatment plan is prevented. A user may be notified that at least one of the one or more treatment fields of the radiation treatment plan is outside the field geometry limits of the class solution corresponding to the at least one collision free region.

In some other embodiments, upon determining that the actual couch coordinate is within at least one collision free region, it may be determined whether the one or more treatment fields of the radiation treatment plan are within the field geometry limits of a class solution corresponding to the at least one collision free region. Upon determining that the one or more treatment fields of the radiation treatment plan are within the field geometry limits of the class solution corresponding to the at least one collision free region, automatic execution of the radiation treatment plan may be enabled.

In some further embodiments, upon determining that the actual couch coordinate is within at least one collision free region, it may be determined whether the one or more treatment fields of the radiation treatment plan are within the field geometry limits of a class solution corresponding to the at least one collision free region. Upon determining that at least one treatment field of the one or more treatment fields of the radiation treatment plan is outside the field geometry limits of the class solution corresponding to the at least one collision free region, the at least one treatment field is removed from the treatment plan, and the radiation treatment plan is executed.

As described above, embodiments of the present invention provide tools for managing collision risks for planning and delivery of radiation treatment. Such tools may increase the robustness of the planning and delivery process especially for non-coplanar treatment. Non-coplanar treatment fields have been increasingly used in cranial and extra-cranial radiosurgery. Higher doses and smaller number of fractions are typically used in radiosurgery. Therefore the dose fall-off from target may need to be sharper in order to avoid excessive dose to critical structures and non-tumorous tissue. The sharper fall-off is normally achieved by more complex field geometries and use of multiple arcs. The time to deliver these more complex treatments is usually longer and collision risks may become more difficult to estimate.

V. Computer System

Figure 18:
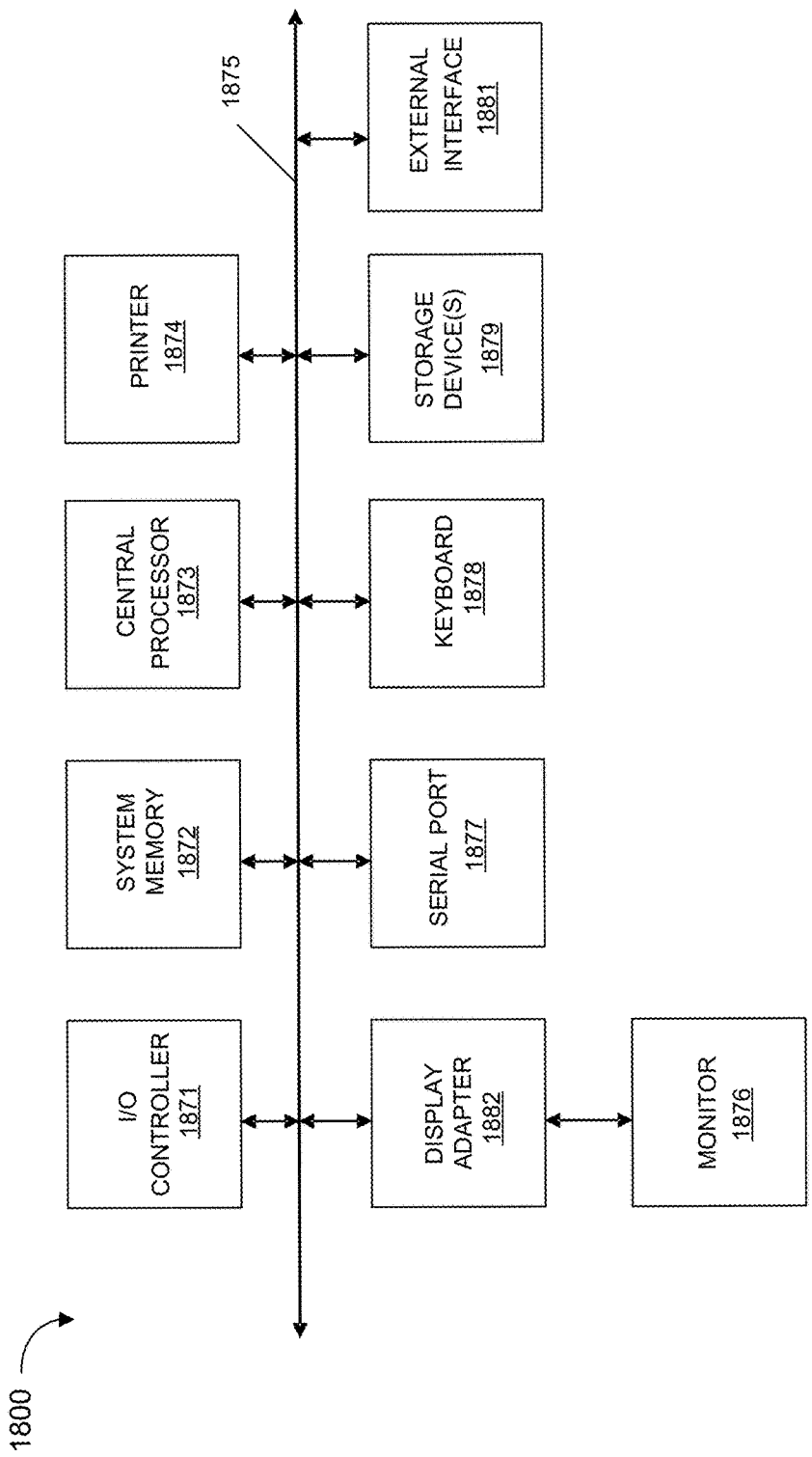
FIG. 18 shows a block diagram of an example computer system usable with system and methods according to embodiments of the present invention.

Any of the computer systems mentioned herein may utilize any suitable number of subsystems. Examples of such subsystems are shown in FIG. 18 in computer system 1800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 18 are interconnected via a system bus 1875. Additional subsystems such as a printer 1874, keyboard 1878, storage device(s) 1879, monitor 1876, which is coupled to display adapter 1882, and others are shown. Peripherals and input/output (I/O) devices, which couple to I/O controller 1871, can be connected to the computer system by any number of means known in the art, such as serial port 1877. For example, serial port 1877 or external interface 1881 (e.g. Ethernet, Wi-Fi, etc.) can be used to connect computer system 1800 to a wide area network such as the Internet, a mouse input device, or a scanner. The interconnection via system bus 1875 allows the central processor 1873 to communicate with each subsystem and to control the execution of instructions from system memory 1872 or the storage device(s) 1879 (e.g., a fixed disk, such as a hard drive or optical disk), as well as the exchange of information between subsystems. The system memory 1872 and/or the storage device(s) 1879 may embody a computer readable medium. Any of the data mentioned herein can be output from one component to another component and can be output to the user.

A computer system can include a plurality of the same components or subsystems, e.g., connected together by external interface 1881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of determining a radiation treatment plan for delivering radiation to a patient using an external-beam radiation treatment system, the method comprising:
   receiving, by a computer system, one or more class solutions, wherein each class solution includes field geometry limits for one or more treatment axes of the external-beam radiation treatment system and a corresponding collision free region, and wherein the collision free region comprises a three-dimensional space for allowed initial isocenter positions determined based on a delivery machine model and a patient model;
   receiving, by the computer system, a three-dimensional image of the patient;
   aligning the three-dimensional image of the patient with the collision free regions of the one or more class solutions;
   receiving, via a user interface, a desired initial isocenter position;
   determining, by the computer system, that the desired initial isocenter position is within at least one collision free region of the one or more class solutions;
   identifying, by the computer system, one or more treatment fields within the field geometry limits of a class solution corresponding to the at least one collision free region; and
   determining, by the computer system, the radiation treatment plan using the one or more identified treatment fields.

2. The method of claim 1, further comprising displaying on the user interface of the computer system the collision free regions of the one or more class solutions and the three-dimensional image of the patient.

3. The method of claim 1, wherein the three-dimensional image of the patient includes image of one or more target volumes within a treatment area of the patient.

4. The method of claim 3, wherein the desired isocenter position is input by a user using an input device of the user interface.

5. The method of claim 3, wherein the desired isocenter position is calculated based on a center of mass of the one or more target volumes or based on a geometrical center point of a smallest box that contains the one or more target volumes.

6. The method of claim 1, wherein:
   each class solution includes one or more predetermined treatment fields;
   determining that the desired isocenter position is within at least one collision free region comprises determining that the desired isocenter position is within a plurality of collision free regions corresponding to a plurality of class solutions; and
   identifying one or more treatment fields comprises selecting a class solution that includes most predetermined treatment fields among the plurality of class solutions, wherein the one or more identified treatment fields include the predetermined treatment fields of the selected class solution.

7. The method of claim 2, wherein:
   the collision free regions are defined relative to a model fixation device;
   the three-dimensional image of the patient is acquired as the patient is fixed to a fixation device, the three-dimensional image including image of the fixation device; and
   the model fixation device is aligned with the image of the fixation device in a display of the collision free regions and the three-dimensional image of the patient.

8. The method of claim 1, wherein the patient model comprises a statistical patient model.

9. The method of claim 1, wherein the radiation treatment plan includes a control-point sequence and a multileaf collimator (MLC) leaf sequence based on the identified one or more treatment fields, and the method further comprising:
   transmitting the radiation treatment plan to control circuitry of the external-beam radiation treatment system to cause the external-beam radiation treatment system to deliver the radiation to the patient according to the control-point sequence and the multileaf collimator (MLC) leaf sequence of the radiation treatment plan.

10. A method of determining a radiation treatment plan for delivering radiation to a patient using an external-beam radiation treatment system, the method comprising:
    receiving, by a computer system, one or more class solutions, wherein each class solution includes field geometry limits for one or more treatment axes of the external-beam radiation treatment system and a corresponding collision free region, and wherein the collision free region comprises a three-dimensional space for allowed initial isocenter positions determined based on a model of a delivery machine and a patient model;
    receiving, by the computer system, a three-dimensional image of the patient;
    aligning the three-dimensional image of the patient with the collision free regions of the one or more class solutions;
    receiving, via a user interface, a desired initial isocenter position;
    receiving, on the user interface, a user selection of one or more treatment fields of the one or more class solutions;
    determining that the desired initial isocenter position is within at least one of the collision free regions;
    identifying a subset of the one or more user-selected treatment fields that are within field geometry limits of a class solution corresponding to the at least one of the collision free regions; and
    determining the radiation treatment plan using the subset of the one or more user-selected treatment fields.

11. The method of claim 10, further comprising displaying on the user interface of the computer system the collision free regions of the one or more class solutions and the three-dimensional image of the patient.

12. The method of claim 10, wherein the subset of the one or more user-selected treatment fields includes all of the one or more user-selected treatment fields.

13. The method of claim 10, wherein identifying the subset of the one or more selected treatment fields comprises:
    for each respective treatment field of the one or more user-selected treatment fields, determining whether the respective treatment field is within the field geometry limits of the class solution corresponding to the at least one of the collision free regions;
    upon determining that the respective treatment field is outside the field geometry limits of the class solution corresponding to the at least one of the collision free regions, excluding the respective treatment field from the subset of the one or more user-selected treatment fields; and
    upon determining that the respective treatment field is within the field geometry limits of the class solution corresponding to the at least one of the collision free regions, including the respective treatment field in the subset of the one or more user-selected treatment fields.

14. The method of claim 10, further comprising:
upon determining that at least one of the one or more user-selected treatment fields is outside the field geometry limits of the class solution corresponding to the at least one of the collision free regions, moving the desired isocenter position to a new isocenter position, wherein the new isocenter position is within another collision free region, and wherein all of the one or more user-selected treatment fields are within field geometry limits of a class solution corresponding to the another collision free region.

15. The method of claim 10, wherein the desired isocenter position is input by a user using an input device of the user interface.

16. The method of claim 10, wherein the desired isocenter position is calculated based on a center of mass of one or more target volumes or based on a geometrical center point of a smallest box that contains the one or more target volumes.

17. A method of delivering radiation to a patient using an external-beam radiation treatment system, the method comprising:
receiving, by a computer system communicably coupled with the external-beam radiation treatment system, one or more class solutions, wherein each class solution includes field geometry limits for one or more treatment axes of the external-beam radiation treatment system and a corresponding collision free region, and wherein the collision free region comprises a three-dimensional space for allowed couch coordinates determined based on a model of a delivery machine and a patient model;
receiving, by the computer system, a radiation treatment plan including one or more treatment fields;
acquiring, by the external-beam radiation treatment system, a three-dimensional image of the patient;
positioning, by the external-beam radiation treatment system, the patient based on the three-dimensional image of the patient to obtain an actual couch coordinate;
determining whether the actual couch coordinate is within at least one collision free region; and
preventing execution of the radiation treatment plan or executing the radiation treatment plan based on whether the actual couch coordinate is within at least one collision free region.

18. The method of claim 17, wherein preventing execution of the radiation treatment plan or executing the radiation treatment plan comprises:
upon determining that the actual couch coordinate is not within any collision free region, preventing execution of the radiation treatment plan.

19. The method of claim 17, wherein preventing execution of the radiation treatment plan or executing the radiation treatment plan comprises:
upon determining that the actual couch coordinate is not within any collision free region, preventing automation of the execution of the radiation treatment plan.

20. The method of claim 17, wherein preventing execution of the radiation treatment plan or executing the radiation treatment plan comprises:
upon determining that the actual couch coordinate is within at least one collision free region, determining whether the one or more treatment fields of the radiation treatment plan are within the field geometry limits of a class solution corresponding to the at least one collision free region;
upon determining that at least one of the one or more treatment fields of the radiation treatment plan is outside the field geometry limits of the class solution corresponding to the at least one collision free region, preventing execution of the radiation treatment plan.

21. The method of claim 20, further comprising:
notifying a user that at least one of the one or more treatment fields of the radiation treatment plan is outside the field geometry limits of the class solution corresponding to the at least one collision free region.

22. The method of claim 17, wherein preventing execution of the radiation treatment plan or executing the radiation treatment plan comprises:
upon determining that the actual couch coordinate is within at least one collision free region, determining whether the one or more treatment fields of the radiation treatment plan are within the field geometry limits of a class solution corresponding to the at least one collision free region;
upon determining that the one or more treatment fields of the radiation treatment plan are within the field geometry limits of the class solution corresponding to the at least one collision free region, enabling automatic execution of the radiation treatment plan.

23. The method of claim 17, wherein preventing execution of the radiation treatment plan or executing the radiation treatment plan comprises:
upon determining that the actual couch coordinate is within at least one collision free region, determining whether the one or more treatment fields of the radiation treatment plan are within the field geometry limits of a class solution corresponding to the at least one collision free region;
upon determining that at least one treatment field of the one or more treatment fields of the radiation treatment plan is outside the field geometry limits of the class solution corresponding to the at least one collision free region, removing the at least one treatment field from the treatment plan; and
executing the radiation treatment plan.

* * * * *